(12) United States Patent
Williams

(10) Patent No.: US 11,229,682 B2
(45) Date of Patent: Jan. 25, 2022

(54) METHODS OF TREATMENT FOR KIDNEY DISEASE

(71) Applicant: Wake Forest University Health Sciences, Winston-Salem, NC (US)

(72) Inventor: James K. Williams, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 16/496,117

(22) PCT Filed: Mar. 29, 2018

(86) PCT No.: PCT/US2018/025063
§ 371 (c)(1),
(2) Date: Sep. 20, 2019

(87) PCT Pub. No.: WO2018/183625
PCT Pub. Date: Oct. 4, 2018

(65) Prior Publication Data
US 2020/0093891 A1 Mar. 26, 2020

Related U.S. Application Data

(60) Provisional application No. 62/478,684, filed on Mar. 30, 2017.

(51) Int. Cl.
*A61K 38/19* (2006.01)
*A61P 13/12* (2006.01)
*A61K 9/00* (2006.01)
*A61K 38/18* (2006.01)
*A61K 47/42* (2017.01)
*A61K 48/00* (2006.01)

(52) U.S. Cl.
CPC .......... *A61K 38/195* (2013.01); *A61K 9/0019* (2013.01); *A61K 38/1866* (2013.01); *A61K 47/42* (2013.01); *A61P 13/12* (2018.01); *A61K 48/00* (2013.01)

(58) Field of Classification Search
None
See application file for complete search history.

(56) References Cited

U.S. PATENT DOCUMENTS

| | | |
|---|---|---|
| 6,352,975 B1 | 3/2002 | Schreiner et al. |
| 7,662,392 B2 | 2/2010 | Itescu |
| 7,776,564 B2 | 8/2010 | Chu et al. |
| 8,435,953 B2 | 5/2013 | Tabata |
| 8,513,007 B2 | 8/2013 | Penn et al. |
| 8,513,213 B2 | 8/2013 | Penn et al. |
| 8,859,613 B2 | 10/2014 | Zicker et al. |
| 2008/0112939 A1 | 5/2008 | Colter et al. |
| 2009/0306625 A1 | 12/2009 | Pereira-Kamath et al. |
| 2010/0247491 A1 | 9/2010 | Westenfelder |
| 2011/0097379 A1* | 4/2011 | Yoo .......... A61L 27/54 424/423 |
| 2012/0289586 A1 | 11/2012 | Penn et al. |
| 2016/0077618 A1 | 3/2016 | An et al. |
| 2016/0303197 A1 | 10/2016 | Sandrasagra et al. |

FOREIGN PATENT DOCUMENTS

WO 2015/171417 11/2015

OTHER PUBLICATIONS

International Search Report and Written Opinion corresponding to PCT/US2018/025063, dated Jun. 14, 2018 (8 pp).
Togel et al. "Role of SDF-1 as a regulatory chemokine in renal regeneration after acute kidney injury" Kidney International Supplements, 1(3):87-89 (2011).
Si et al. "Transforming growth facor-ß1 promotes homing of bone marrow mesenchymal stem cells in renal ischemia-reperfusion injury" International Journal of Clinical & Experimental Pathology, 8(10):12368-12378 (2015).
International Search Report and Written Opinion corresponding to PCT/US2018/025033, dated Jun. 14, 2018 (8 pp).
D'Apuzzo et al. "The chemokine SDF-1, stromal cell-derived factor 1, attracts early stage B cell precursors via the chemokine receptor CXCR4" European Journal of Immunology, 27(7):1788-1793 (1997) (Abstract only).
Chade et al. "Reversal of renal dysfunction by targeted administration of VEGF into the stenotic kidney: a novel potential therapeutic approach" Am J Physiol Renal Physiol, 302(10):F1342-F1350 (2012).
Polzin et al. "Dietary management of feline chronic renal failure: where are we now? In what direction are we headed?" Journal of Feline Medicine & Surgery, 2(2):75-85 (2000) (Abstract only).
Chakrabarti et al. "Clinicopathological Variables Predicting Progression of Azotemia in Cats with Chronic Kidney Disease" Journal of Veterinary Internal Medicine, 26(2):275-281 (2012).
King et al. "Tolerability and Efficacy of Benazepril in Cats with Chronic Kidney Disease" Journal of Veterinary Internal Medicine, 20(5):1054-1064 (2006).
Mizutani et al. "Evaluation of the Clinical Efficacy of Benazepril in the Treatment of Chronic Renal Insufficiency in Cats" Journal of Veterinary Internal Medicine, 20(5):1074-1079 (2006).
Jepson at al. "Effect of Control of Systolic Blood Pressure on Survival in Cats with Systemic Hypertension" Journal of Veterinary Internal Medicine, 21(3):402-409 (2007).
Lau et al. "Stromal cell-derived factor-1 (SDF-1): homing factor for engineered regenerative medicine" Expert Pinion on Biological Therapy, 11(2): 189-197 (2011) (Abstract only).
Herberg al. "Stromal Cell-Derived Factor-1ß Mediates Cell Survival through Enhancing Autophagy in Bone Marrow-Derived Mesenchymal Stem Cells" PLoS One, 8(3):e58207 (2013).

(Continued)

*Primary Examiner* — Marianne P Allen
(74) *Attorney, Agent, or Firm* — Myers Bigel, P.A.

(57) ABSTRACT

The present disclosure provides compositions and methods for treatment of a kidney disease with chemokine protein stromal cell-derived factor 1 (SDF-1), such as methods of treating a subject afflicted with or at risk of developing a kidney disease, comprising administering SDF-1 to a kidney of the subject in a treatment-effective amount.

15 Claims, 1 Drawing Sheet

(56) References Cited

OTHER PUBLICATIONS

Ara et al. "Long-Term Hematopoietic Stem Cells Require Stromal Cell-Derived Factor-1 for Colonizing Bone Marrow during Ontogeny" Immunity, 19(2):257-267 (2003) (Abstract only).

Zisa et al. "Intramuscular VEGF activates an SDF1-dependent progenitor cell cascade and an SDF1-independent muscle paracrine cascade for cardiac repair" Am J Physiol Heart Circ Physiol, 301(6):H2422-H2432 (2011).

Schmiedt et al. "Unilateral Renal Ischemia as a Model of Acute Kidney Injury and Renal Fibrosis in Cats" Veterinary Pathology, 53(1):87-101 (2016).

Chen et al. "Homing of endogenous stem/progenitor cells for in situ tissue regeneration: Promises, strategies, and translational perspectives" Biomaterials, 32(12):3189-3209 (2011).

Ghadge et al. "SDF-1a as a therapeutic stem cell homing factor in myocardial infarction" Pharmacology & Therapeutics, 129(1):97-108 (2011).

Ohnishi et al. "Stromal cell-derived factor-1 (SDF1)-dependent recruitment of bone marrow-derived renal endothelium-like cells in a mouse model of acute kidney injury" Clinical Pathology, 77(3):313-319 (2015).

Kim et al. "Enhancing neurogenesis and angiogenesis with target delivery of stromal cell derived factor-1a using a dual ionic pH-sensitive copolymer" Biomaterials, 61:115-125 (2015).

Williams et al. "Regenerative pharmacology: recent developments and future perspectives" Regernerative Medicine, 11(8):859-870 (2016).

Extended European Search Report corresponding to EP 18777904; dated Dec. 11, 2020 (7 pages).

Alexandre, Cristianne Silva, et al., "Lineage-Negative Bone Marrow Cells Protect Against Chronic Renal Failure", Stem Cells, 27(3), 2009, 682-692.

Baptist Medical Center, Wake Forest University , "You are not a cat, but a cat could someday help treat your chronic kidney disease", Medical Xpress, retried Mar. 16, 2021 from https://medicalxpress.com/news/2021-03-cat-chronic-kidney-disease.html, 2 pp.

Bennington, Julie , et al., "Chemokine Therapy in Cats With Experimental Renal Fibrosis and in a Kidney Disease Pilot Study", Frontier in Veterinary Science, vol. 8, Article 646087, 2021, 1-13.

Bogoslovsky, Tanya , et al., "Stromal-Derived Factor-1α Correlates With Circulating Endothelial Progenitor Cells and With Acute Lesion Volume in Stroke Patients", Stroke 42(3), 2011, 618-625.

Bromage, Daniel I., et al., "Stromal cell-derived factor-1α signals via the endothelium to protect the heart against ischaemia-reperfusion injury", Journal of Molecular and Cellular Cardiology 128, 2019, 187-197.

Chen, Li-Hao , et al., "SDF-1/CXCR4 Signaling Preserves Microvascular Integrity and Renal Function in Chronic Kidney Disease", PLoS ONE 9(3), 2014, e92227.

Drury, Luke J., et al., "Monomeric and dimeric CXCL12 inhibit metastasis through distinct CXCR4 interactions and signaling pathways", PNAS 108(43), 2011, 17655-17660.

Ersoy, Gulcin Sahin, et al., "CXCL12 Promotes Stem Cell Recruitment and Uterine Repair after Injury in Asherman's Syndrome", Molecular Therapy—Methods & Clinical Development 4, 2017, 169-177.

Floranovićv, Milena POTIć, et al., "Effect of CXCL12 and Its Receptors on Unpredictable Renal Cell Carcinoma", Clinical Genitourinary Cancer 18(4), 2020, e337-e342.

Gao, Jia-Hui, et al., "CXC chemokine ligand 12 (CXCL12) in atherosclerosis: An underlying therapeutic target", Clinica Chimica Acta 495, 2019, 538-544.

Janssens, Rik , et al., "The unique structural and functional features of CXCL12", Cellular & Molecular Immunology 15(4), 2018, 299-311.

Khalifa, Ahmad O., et al., "Stromal derived factor-1 plasmid as a novel injection for treatment of stress urinary incontinence in a rat model", International Urogynecology Journal 31(1), 2020, 107-115.

Klimczak-Tomaniak, D. , et al., "CXCL12 in Patients with Chronic Kidney Disease and Healthy Controls: Relationships to Ambulatory 24-Hour Blood Pressure and Echocardiographic Measures", Cardiorenal Med. 8(3), 2018, 249-258.

Liu, Yahong , et al., "C-X-C motif chemokine receptor 4 aggravates renal fibrosis through activating JAK/STAT/GSK3β/β-catenin pathway", Journal of Cellular and Molecular Medicine 24(7), 2020, 3837-3855.

Mo, Hongyan , et al., "C-X-C Chemokine Receptor Type 4 Plays a Crucial Role in Mediating Oxidative Stress-Induced Podocyte Injury", Antioxidants & Redox Signaling 27(6), 2017, 345-362.

Patalano, Susan , et al., "CXCL12/CXCR4-Mediated Procollagen Secretion Is Coupled To Cullin-RING Ubiquitin Ligase Activation", Scientific Reports 8(article 3499), 2018, 11 pages.

Ray, Paramita , et al., "Secreted CXCL12 (SDF-1) forms dimers under physiological conditions", Biochem J 442(2), 2012, 433-442.

Rodríguez-Nieves, JOSé A., et al., "CXCL12/CXCR4 Axis Activation Mediates Prostate Myofibroblast Phenoconversion through Non-Canonical EGFR/MEK/ERK Signaling", PLoS ONE 11(7), 2016, e0159490.

Romoli, Simone , et al., "CXCL12 blockade preferentially regenerates lost podocytes in cortical nephrons by targeting an intrinsic podocyte-progenitor feedback mechanism", Kidney International 94(6), 2018, 1111-1126.

Stokman, Geurt , et al., "SDF-1 provides morphological and functional protection against renal ischaemia/reperfusion injury", Nephrology Dialysis Transplantation, 25(12), 2010, 3852-3859.

Sun, Zejia , et al., "Stromal cell-derived factor-1/CXC chemokine receptor 4 axis in injury repair and renal transplantation", The Journal of International Medical Research 47(11), 2019, 5426-5440.

Takabatake, Yoshitsugu , et al., "The CXCL12 (SDF-1)/CXCR4 Axis Is Essential for the Development of Renal Vasculature", Journal of the American Society of Nephrology 20(8), 2009, 1714-1723.

Veldkamp, Christopher T., et al., "Monomeric structure of the cardioprotective chemokine SDF-1/CXCL12", Protein Science 18(7), 2009, 1359-1369.

Veldkamp, Christopher T., et al., "Structural Basis of CXCR4 Sulfotyrosine Recognition by the Chemokine SDF-1/CXCL12", Science Signaling 1(37), 2008, ra4.

Williams, J. Koudy, et al., "Cell Versus Chemokie Therapy Effects on Cell Mobilization to Chronically Dysfunctional Urinary Sphincters of Nonhuman Primates", International Neurourology Journal 22(4), 2018, 260-267.

Williams, J. Koudy, et al., "Cell versus Chemokine Therapy in a Nonhuman Primate Model of Chronic Intrinsic Urinary Sphincter Deficiency", The Journal of Urology 196(6), 2016, 1809-1815.

Williams, J. Koudy, et al., "Efficacy and Initial Safety Profile of CXCL12 Treatment in a Rodent Model of Urinary Sphincter Deficiency", Stem Cells Translational Medicine 6(8), 2017, 1740-1746.

Zambon, Joao P., et al., "Nonhuman primate model of persistent erectile and urinary dysfunction following radical prostatectomy: Feasibility of minimally invasive therapy", Neurourology and Urodynamics 37(7), 2018, 2141-2150.

* cited by examiner

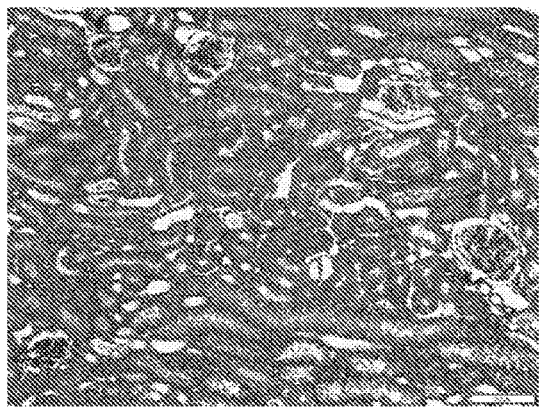
FIG. 1A 100 μm
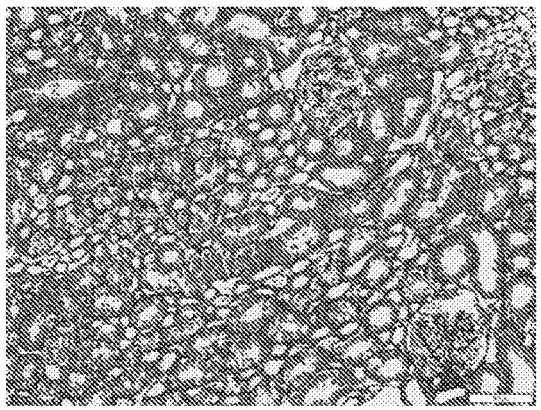
FIG. 1B 100 μm
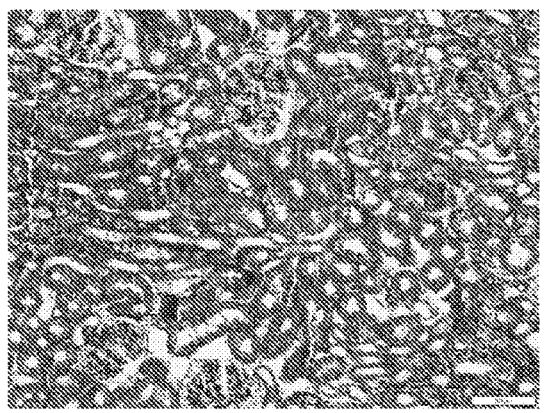
FIG. 1C 100 μm
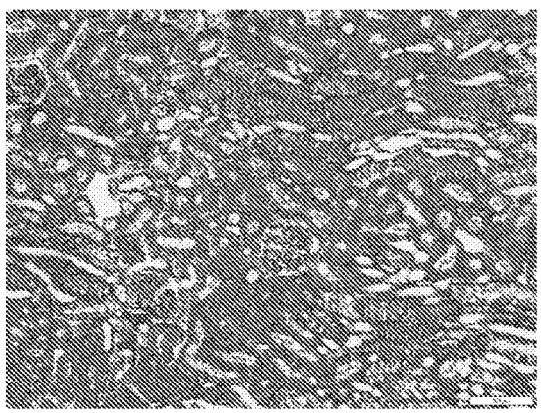
FIG. 1D 100 μm

METHODS OF TREATMENT FOR KIDNEY DISEASE

CROSS REFERENCE TO RELATED APPLICATIONS

This application is a 35 § 371 national phase application of International Application Serial No. PCT/US2018/025063, filed Mar. 29, 2018, which claims the benefit of U.S. provisional patent application Ser. No. 62/478,684, filed Mar. 30, 2017, the disclosure of which is incorporated by reference herein in its entirety.

BACKGROUND

Chronic kidney disease (CKD), also known as chronic renal disease or chronic renal failure, is a progressive loss in renal function over a period of months or years. CKD can be caused by a variety of conditions and mechanisms, and affects humans as well as other animals, such as companion animals. For example, CKD is one of the most common causes of illness and death in geriatric cats.

New treatment options are needed for the treatment of kidney disease.

SUMMARY

Provided herein is a method of treating a subject afflicted with or at risk of developing a kidney disease, including administering stromal cell-derived factor 1 (SDF-1) to the subject (e.g., to the kidney of the subject) in a treatment-effective amount. In some embodiments, the kidney disease is acute renal failure, chronic kidney disease, end-stage renal disease, or anemia. In some embodiments, the kidney disease is chronic interstitial nephritis.

In some embodiments, the method further comprises administering to said subject an angiogenic growth factor (e.g., vascular endothelial growth factor (VEGF)) in combination with said SDF-1.

Further provided is a sterile injectable composition for the treatment of a kidney disease, comprising: SDF-1 and an aqueous carrier. In some embodiments, the composition comprises collagen or gelatin. In some embodiments, the composition further comprises an angiogenic growth factor (e.g., vascular endothelial growth factor (VEGF)).

Also provided is SDF-1 or a vector encoding SDF-1 as described herein for use in carrying out a method of treating a subject afflicted with or at risk of developing a kidney disease, or for use in the preparation of a medicament for carrying out a method of treating a subject afflicted with or at risk of developing a kidney disease.

BRIEF DESCRIPTION OF THE DRAWINGS

FIG. 1A-FIG. 1D present histology (Masson's trichrome staining) of kidney tissues of the different control and treatment groups.

FIG. 1A presents histology of kidney tissue from a control subject.

FIG. 1B presents histology of kidney tissue from an injured subject without treatment.

FIG. 1C presents histology of kidney tissue from an injured subject receiving injection of the carrier.

FIG. 1D presents histology of kidney tissue from an injured subject receiving injection of SDF-1 in the carrier.

The administration of SDF-1 restores more normal corticomedullary architecture to the tissue.

DETAILED DESCRIPTION OF EMBODIMENTS

The present disclosure provides compositions and methods for treatment of a kidney disease with chemokine protein stromal cell-derived factor 1 (SDF-1).

The disclosures of all patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise. As used herein, "and/or" and "/" refer to and encompass any and all possible combinations of one or more of the associated listed items, as well as the lack of combinations when interpreted in the alternative ("or").

"Treat" as used herein refers to any type of treatment that imparts a benefit to a subject or patient, particularly the improvement of kidney function, delaying or retarding onset or progression or worsening of a deficiency in kidney function, or a sign or symptom thereof, etc.

"Pharmaceutically acceptable" as used herein means that the compound or composition is suitable for administration to a subject, without unduly deleterious side effects in light of the severity of the disease and necessity of the treatment.

"Kidney disease" refers to any type of disease or disorder that may compromise one or more kidney functions, including, but not limited to, acute renal failure (e.g., caused by poison, trauma, shock, infection, blockage such as kidney stones, heart failure, etc.), chronic kidney disease (CKD) (e.g., gradual loss of kidney function due to aging, genetics, blockage such as kidney stones, diabetes, infection, dental disease, immunological disease, high blood pressure, thyroid disorder, cancer, congenital kidney malformation, congenital polycystic kidney disease, etc.), end-stage renal disease, anemia, etc. As an example, interstitial nephritis (inflammation of the interstitium of the kidneys surrounding the tubules) may be acute interstitial nephritis or chronic interstitial nephritis, which may eventually lead to kidney failure.

"Subject" or "patient" as used herein generally refers to animal subjects susceptible to kidney disease, including both human subjects and non-human animal subjects (e.g., dog, cat, horse, bird, etc.) for research or veterinary purposes. Subjects may be male or female and may be of any suitable age, including neonate, infant, juvenile, adolescent, adult, and geriatric subjects.

1. Active Compounds.

The active compound used herein is chemokine protein stromal cell-derived factor 1 (SDF-1). The compound is also known as the C-X-C motif chemokine 12 (CXCL12), and in humans it is encoded by the CXCL12 gene. SDF-1 is known and described in, for example, M. D'Apuzzo et al., The chemokine SDF-1, stromal cell-derived factor 1, attracts early stage B cell precursors via the chemokine receptor CXCR4, *Eur. J. Immunol.* 27, 1788-1793 (1997); Y. Tabata, U.S. Pat. No. 8,435,953, and Penn et al., U.S. Pat. Nos. 8,513,213 and 8,513,007; and S. Itescu, U.S. Pat. No. 7,662,392, the disclosures of which are incorporated by reference herein in their entirety. See also J. K. Williams, WO 2015/171417.

As used herein, SDF-1 may include isoforms and mature forms thereof, such as, e.g., SDF-1β, SDF-1γ, SDF-1δ, SDF-1ε and SDF-1φ, in addition SDF-1α or a mature form thereof, or a mixture thereof in an arbitrary ratio or the like.

SDF-1 in the present invention includes SDF-1α, SDF-1β, a mixture thereof in an arbitrary ratio or the like. See U.S. Pat. No. 8,435,953.

In the present invention, so long as SDF-1 has activity as a chemokine, SDF-1 may be substituted, deleted and/or added by one or plural amino acid(s) in the amino acid sequence. Similarly, it may be substituted, deleted and/or added by a sugar chain. SDF-1 may form a salt (preferably, an acid addition salt) with a physiologically acceptable acid (for example, an inorganic acid or an organic acid) or a base (for example, an alkali metal salt). Examples of the salt include a salt with an inorganic acid (for example, hydrochloric acid, phosphoric acid, hydrobromic acid, or sulfuric acid) and a salt with an organic acid (for example, acetic acid, formic acid, propionic acid, fumaric acid, maleic acid, succinic acid, tartaric acid, citric acid, malic acid, oxalic acid, benzoic acid, methanesulfonic acid, or benzenesulfonic acid).

SDF-1 used in the present invention may be derived from mammals such as human or non-human animals such as monkey, sheep, cow, horse, pig, dog, cat, rabbit, rat, or mouse. For example, in some embodiments when the composition of the present invention is for use in a human, the composition of the present invention may be produced using human SDF-1 (for example, SDF-1α (GeneBank Accession No. NP_954637) or SDF-1β (GeneBank Accession No. NP_000600)). As another example, in some embodiments when the composition is for use in a domestic cat, the composition of the present invention may be produced using cat SDF-1 (for example, GeneBank Accession No. NP_001009847 (*Felis catus*)). As a further example, in some embodiments, when the composition is for use in a domestic dog, the composition of the present invention may be produced using dog SDF-1 (for example, GeneBank Accession No. AAU89475 (*Canis lupus familiaris*) or GeneBank Accession No. NP_001121569 (*Canis lupus familiaris*)).

In some embodiments, SDF-1 may be purified to a level at which the action of SDF-1 is not inhibited by other contaminants. Preferably, SDF-1 may be purified to be usable as a pharmaceutical preparation.

In the present invention, SDF-1 may be obtained from natural sources or produced by a genetic engineering technique. When obtained from natural sources, SDF-1 may be extracted from various organs such as the spleen of mammals such as human or non-human animal (for example, monkey, sheep, cow, horse, dog, cat, rabbit, rat, or mouse), in which SDF-1 is already known to exist. To give a specific example of an organ in which SDF-1 is known to exist, for example, SDF-1 is known to be present in a large amount in organs in which tumor cells expressing CXCR4, a SDF-1 receptor, transfer with high frequency. On the other hand, when produced by a genetic engineering technique, a gene coding SDF-1 from a mammal such as human or non-human animals (for example, monkey, sheep, cow, horse, pig, dog, cat, rabbit, rat, or mouse) is incorporated into a suitable vector, which is introduced into a suitable host cell for transformation, to thereby be able to obtain the target recombinant SDF-1 from a culture supernatant of the transformant. The host cell herein is not limited and various host cells such as *E. coli,* yeast cells, various insect cells such as silkworm cells and various animal cells, which have been normally used in the genetic engineering techniques, may be used.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

In some embodiments, the SDF-1 may be administered directly onto and/or into kidney tissue, e.g., by injection, or by administering (e.g., by injection) a nucleic acid vector (e.g., integrating and non-integrating viral vectors, retroviral vectors, plasmid vectors, linear DNA vectors, etc.) that encodes SDF-1 and expresses (e.g., transiently or constitutively expresses) SDF-1 in the kidney tissue. In general, such vectors comprise a nucleic acid segment encoding SDF-1 as described above operatively associated with a promoter (e.g., a CMV promoter) that is operable in the tissue. Suitable vectors, including plasmid vectors, are known or will be apparent to those skilled in the art based on the present disclosure and include but are not limited to the plasmid deposited with the American Type Culture Collection under accession number PTA-13320, as described in, for example, Penn et al., U.S. Pat. Nos. 8,513,213 and 8,513,007, the disclosures of which are incorporated by reference herein.

2. Pharmaceutical Formulations.

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Non-limiting examples of a sterile carrier include endotoxin-free or pyrogen-free water or saline.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well-known in the art.

The pharmaceutical compositions may be formulated for immediate release, and/or sustained release of SDF-1, for example, in a sustained release composition containing a hydrogel with modified gelatin having a carboxyl group and/or a sulfo group. See, e.g., U.S. Pat. No. 8,435,953 to Tabata. In some embodiments, the composition may include collagen and/or gelatin.

3. Dosage and Routes of Administration.

As noted above, the present invention provides pharmaceutical formulations comprising the active compounds (including the pharmaceutically acceptable salts thereof), in pharmaceutically acceptable carriers for parenteral administration.

Direct organ administration (e.g., direct injection onto and/or into one or more portions of the kidney) may be carried out by any suitable technique. Administration by injection may be done by continuous infusion or by single or multiple boluses. See, e.g., U.S. Patent Application Publication No. 2009/0306625 to Pereira-Kamath et al.

In some embodiments, direct organ administration may be guided by imaging techniques, for example, by ultrasound guidance. In some embodiments, the administration is by direct administration (e.g., direct injection or infusion) into one or multiple sites in the mid-renal cortex (e.g., from 1, 2 or 3 to 7, 8, 9 or 10 sites). In some embodiments, the administration is by intraarterial infusion into the kidney.

The therapeutically effective dosage of any specific compound, the use of which is in the scope of present invention, may vary somewhat from compound to compound, and patient to patient, and will depend upon the condition of the patient and the route of delivery. In general, for direct organ injection of SDF-1, an amount of from about 10 or 50 nanograms to 400, 800 or 1000 nanograms per administration, or an amount of from about 10 or 50 micrograms to 400, 800 or 1000 micrograms per administration, depending upon the subject (e.g., human or companion animal subject) may be appropriate, with each subject receiving one injection into organ tissue per treatment session, or a plurality of injections (e.g., 2, 3, 4, 5, 6) into organ tissue at different sites therein (e.g., sites distributed around the organ or a portion thereof (e.g., around the dorsal pole of the kidney)) in each treatment session.

Treatment sessions may be repeated periodically as deemed appropriate (e.g., once every two or four months). Where a nucleic acid vector is administered, the vector can be administered in an amount effective to achieve corresponding levels of expression of the SDF-1 in or near the injection site.

4. Combination Therapy.

In some embodiments, SDF-1 is administered in combination with an angiogenic growth factor (e.g., vascular endothelial growth factor (VEGF)). See, e.g., U.S. Pat. No. 6,352,975 to Schreiner et al.; Chade et al., Reversal of renal dysfunction by targeted administration of VEGF into the stenotic kidney: a novel potential therapeutic approach. Am J Physiol Renal Physiol 2012 May 15; 302(10):F1342-50; US Patent Application Publication No. 2016/077618 to Chade et al.

The administration of two or more agents, such as SDF-1 and VEGF, "in combination" means that the two agents are administered closely enough in time that the presence of one alters the biological effects of the other. The two may be applied simultaneously (concurrently or contemporaneous) or sequentially. Administrations according to some embodiments may be within a period of time that ranges from minutes (e.g., 1, 5, 10, 30, 60, or 90 minutes or more) to days (e.g., 1, 2, 5, 8 or 10 or more days), as appropriate for efficacious treatment.

Simultaneous, concurrent or contemporaneous administration may be carried out by mixing the agents into the same composition prior to administration, or by administering the agents at the same point in time but at different sites of the body or organ or using different types of administration, or applied at times sufficiently close that the results observed are essentially the same as those achieved when the agents are administered at the same point in time.

Sequential application of the agents may be carried out by administering one agent at some point in time prior to administering another agent, such that the prior administration enhances the effects of the subsequent administration.

SDF-1, optionally in combination with VEGF, may also be administered in combination with one or more other treatments, e.g., fluid therapy to address dehydration, surgery to remove blockages, antibiotics to treat an infection, angiotension converting enzyme (ACE) inhibitors to control hypertension, dietary restrictions (e.g., diet low in protein, phosphorus, calcium and/or sodium) and/or supplements (e.g., phosphorus binders, vitamin D supplements), etc. For example, supplements such as antioxidants, mitochondrial cofactors, may be provided in a food composition. See U.S. Pat. No. 8,859,613 to Zicker et al.

The present invention is explained in greater detail in the following non-limiting Examples.

EXAMPLE 1

Chronic kidney disease (CKD) affects an estimated 1% to 3% of all cats. Prevalence of feline CKD increases with age, with as many as 30% to 50% of cats older than 15 years of age have CKD, and the prevalence of CKD appears to be increasing.

Treatment for CKD in cats is largely palliative. In the earlier stages of CKD, dietary changes that reduce serum phosphorus concentrations are effective in restoring serum markers of CKD (Polzin et al. Dietary management of feline chronic renal failure. Where are we now? In what direction are we headed? J Feline Med Surg 2000; 2:75-82). As the disease progresses, angiotensin-converting enzyme inhibitors and calcium-channel blockers are used to reduce proteinuria and normalize systemic and intra-glomerular blood pressure (Chakrabarti et al. Clinicopathological variables predicting progression of azotemia in cats with chronic kidney disease. J Vet Intern Med 2012; 26:275-281; King et al. Tolerability and efficacy of benazepril in cats with chronic kidney disease. J Vet Intern Med 2006; 20:1054-1064; Mizutani et al. Evaluation of the clinical efficacy of benazepril in the treatment of chronic renal insufficiency in cats. J Vet Intern Med 2006; 20:1074-1079; Jepson et al. Effect of control of systolic blood pressure on survival in cats with systemic hypertension. J Vet Intern Med 2007; 21:402-409). In later stages of CKD, treatment tends to focus on limiting clinical signs associated with decreased renal function. While these treatments can extend life and provide a higher quality of life, they do not provide a cure.

The chemokine CXCL12 (sometimes called stromal derived factor-1 or SDF-1) effects cell trafficking and homing of progenitor cells to sites of injury through a receptor (CXCR4/CXCR7) mechanism and enhancing cell survival once at the injury site (Nagasawa, CXC chemokine ligand 12 (CXCL12) and its receptor CXCR4. J Mol Med (Berl). (2014) 92(5), 433-9; Lau et al., Stromal cell-derived factor-1 (SDF-1): homing factor for engineered regenerative medicine. Expert Opin Biol Ther. (2011)11(2), 189-97; Herberg et al. Stromal cell-derived factor-1β mediates cell survival through enhancing autophagy in bone marrow-derived mesenchymal stem cells. PLoS One. (2013) 8(3), e58207; Ara et al. Long-term hematopoietic stem cells require stromal cell-derived factor-1 for colonizing bone marrow during ontogeny. Immunity. (2003) 19(2), 257-67; Zisa et al. Intramuscular VEGF activates an SDF1-dependent progenitor cell cascade and an SDF1-independent muscle paracrine cascade for cardiac repair. Am J Physiol Heart Circ Physiol (2011) 6: 2422-243). One group has reported that CXCL12 was involved in recruitment of bone marrow cells to the kidney in a mouse model of acute kidney injury.

Methods

CXCL12 is administered directly to the kidneys of cats with experimentally-produced chronic kidney disease.

Safety and Feasibility Study. This study utilizes 6 adult female cats. Three of the cats receive carrier injections only (no CXCL12) injected at 5 locations (0.25 ml each) along the dorsal pole of the left kidney at equal distances from one another (probably around 1 cm apart). These injections will be made at the level of the mid-kidney cortex. Three other cats receive the same injections except with 40 ng/human recombinant CXCL12 (added to the carrier solution—saline) injected at the same sites with a total of 200 ng CXCL12. The injections are ultrasound guided and injected into the mid-renal cortex.

CBC, BUN, Creatinine, urinalysis, SDMA test kit from IDEXX (for testing glomeruli-filtration and kidney function) are assessed prior to injection. This is used as a replacement for and is highly correlated with standard GFR (filtration rates). These measures will be repeated 4 weeks post injected and then again 4 weeks later.

Efficacy Study. This study includes 14 adult female cats. Two will be untouched controls. There are three treatment groups: 1) induced unilateral CKD/no treatment (n=4); 2) induced CKD/carrier injection (n=4); and 3) induced CKD/carrier plus CXCL12 injection (n=4).

Induce an ischemia/reperfusion injury to the left kidney. The blood and urine evaluations are repeated at 4 weeks and 8 weeks post injury when the kidneys are injected as described above for the safety study. Blood and urine analysis are repeated 4 and 8 weeks post injection. CBC, BUN, Creatinine, urinalysis, SDMA (for testing glomeruli-filtration and kidney function) are assessed.

Creation of CKD in Cats. The procedure published by Schmiedt et al. is used (Unilateral Renal Ischemia as a Model of Acute Kidney Injury and Renal Fibrosis in Cats. Vet Pathol. 2016 January; 53(1):87-101). Injections are made at the level of the mid-kidney cortex, as described above.

EXAMPLE 2

Four Groups were tested: SDF-1(4), Carrier(4), No Tx(4), Control(1). A CKD Model was surgically created in the cats as described above (n=12). Retroperitoneal injections of 200 ng total dosage were performed into the Left Kidney (n=6) under ultrasound guidance, with three injections of 66.7 ng each into the Left Renal Cortex.

Results

TABLE 1

Volume % Comparison of Left Kidney vs. Right Kidney

| GROUP | VOLUME % |
| --- | --- |
| No Injury Control (no injection) | 91.2% |
| Injury Carrier (injection) | 83.9% |
| Injury SDF-1 (injection) | 99.6% |
| Injury No Tx (no injection) | 101.9% |

TABLE 2

Renal Parameters: Average by Group

| | SDMA | Creat | BUN | Phos | USG | Proteinuria |
| --- | --- | --- | --- | --- | --- | --- |
| CXCL12 | | | | | | |
| 8 wk post injury (4) | 16.75 | 1.20 | 25.75 | 6.13 | 1.047 | 0 |
| 8 wk post tx (4) | 16.00 | 1.30 | 25.75 | 5.15 | 1.047 | 0 |
| Carrier | | | | | | |
| 8 wk post injury (4) | 15.75 | 1.20 | 25.50 | 5.75 | 1.047 | 0 |
| 8 wk post tx (4) | 13.75 | 1.30 | 28.50 | 5.85 | 1.044 | 0 |
| Control | | | | | | |
| 8 wk post injury (1) | 13 | 1.4 | 23 | 5.5 | 1.050 | 0 |
| 8 wk post tx (1) | 11 | 1.3 | 25 | 5.3 | 1.052 | 0 |
| No Tx | | | | | | |
| 8 wk post injury (4) | 13.50 | 1.28 | 26.00 | 6.50 | 1.044 | 0 |
| 8 wk post tx (4) | 12.25 | 1.4 | 29.25 | 6.13 | 1.046 | 0 |

TABLE 3

Renal Parameters: Average by Group, Minus Outliers

|  | SDMA | Creat | BUN | Phos | USG | Proteinuria |
|---|---|---|---|---|---|---|
| CXCL12 | | | | | | |
| 8 wk post injury (3) | 16.67 | 1.23 | 26.33 | 6.4 | 1.050 | 0 |
| 8 wk post tx (3) | 17 | 1.33 | 27 | 5.33 | 1.046 | 0 |
| Carrier | | | | | | |
| 8 wk post injury (3) | 16.33 | 1.27 | 26.67 | 6.03 | 1.047 | 0 |
| 8 wk post tx (3) | 12.67 | 1.37 | 29 | 5.73 | 1.045 | 0 |
| Control | | | | | | |
| 8 wk post injury (1) | 13 | 1.4 | 23 | 5.5 | 1.050 | 0 |
| 8 wk post tx (1) | 11 | 1.3 | 25 | 5.3 | 1.052 | 0 |
| No Tx | | | | | | |
| 8 wk post injury (3) | 12.33 | 1.13 | 24.33 | 6.47 | 1.048 | 0 |
| 8 wk post tx (3) | 12.33 | 1.37 | 26.67 | 6.07 | 1.046 | 0 |

Conclusions

There were beneficial effects of CXCL12 on kidney volume, and on blood and urine measures. However, injection of carrier, which contained collagen (see WO 2015/171417), may cause some renal pathology and/or some adverse changes in these measures. Histologic analysis shown in FIG. 1A-FIG. 1D evidence that injury results in kidney cortico-medullary, fibrosis and cell damage, and that SDF-1 (CXCL12) restores more normal cortico-medullary architecture. The results are encouraging, but not yet statistically significant because of small numbers of animals tested.

The foregoing is illustrative of the present invention, and is not to be construed as limiting thereof. The invention is defined by the following claims, with equivalents of the claims to be included therein.

What is claimed is:

1. A method of treating a subject afflicted with a chronic kidney disease, comprising administering mammalian stromal cell-derived factor 1 alpha (SDF-1α) to a kidney of the subject in a treatment-effective amount,
    wherein said administering step is carried out by direct injection of the SDF-1α into said kidney, and
    wherein said administering of the treatment-effective amount of SDF-1α a results in decreased cellular disruption and/or decreased fibrosis of the kidney.

2. The method of claim 1, wherein said subject is a human subject.

3. The method of claim 1, wherein said subject is a non-human mammalian subject.

4. The method of claim 1, wherein said subject is a cat, a dog, or a horse.

5. The method of claim 1, wherein said subject is a domestic cat.

6. The method of claim 1, wherein said chronic kidney disease comprises chronic interstitial nephritis.

7. The method of claim 1, wherein said SDF-1α is provided in a pharmaceutically acceptable carrier.

8. The method of claim 7, wherein said pharmaceutically acceptable carrier is sterile.

9. The method of claim 1, wherein said direct injection is carried out at a plurality of sites on and/or within the kidney.

10. The method of claim 1, wherein said SDF-1α is human SDF-1α.

11. The method of claim 1, wherein said SDF-1α is cat SDF-1α or dog SDF-1α.

12. The method of claim 1, wherein said method further comprises administering to said subject an angiogenic growth factor in combination with said SDF-1α.

13. The method of claim 1, wherein said SDF-1α is recombinant SDF-1α.

14. The method of claim 1, wherein said SDF-1α is human recombinant SDF-1α.

15. The method of claim 14, wherein said subject is a domestic cat.

* * * * *